US005571334A

United States Patent [19]
Dunn et al.

[11] Patent Number: 5,571,334
[45] Date of Patent: Nov. 5, 1996

[54] STARCH-BASED OPACIFYING AGENT FOR FOODS AND BEVERAGES

[75] Inventors: John M. Dunn, Sioux City, Iowa; Akiva T. Gross, Newton; Eugene T. Finocchiaro, Milton, both of Mass.

[73] Assignee: Opta Food Ingredients, Inc., Bedford, Mass.

[21] Appl. No.: 413,507

[22] Filed: Mar. 30, 1995

Related U.S. Application Data

[63] Continuation-in-part of Ser. No. 221,178, Mar. 31, 1994, abandoned.

[51] Int. Cl.⁶ .......................... C08B 30/00; C08B 30/12; C13F 3/00; A23L 1/05
[52] U.S. Cl. .................. 127/70; 127/29; 127/32; 426/661
[58] Field of Search .................. 127/29, 32, 70; 426/661

[56] References Cited

U.S. PATENT DOCUMENTS 5,089,171  2/1992  Chiu ............................ 52/315.3
5,194,284  3/1993  Chiu et al. .................... 426/589

Primary Examiner—Glenn A. Caldarola
Assistant Examiner—Patricia L. Hailey
Attorney, Agent, or Firm—Hamilton, Brook, Smith & Reynolds, P.C.

[57] ABSTRACT

The present invention pertains to a novel starch-based opacifying agent, to methods of manufacture and to food and non-food formulations containing the opacifying agent. The starch-based opacifying agent comprises an opacifier (e.g., titanium dioxide) and starch in the form of a complex in which the opacifier has been stabilized or entrapped therein. The opacifying agent can be used in low fat and fat-free foods and beverages, including coffee creamer, cottage cheese dressing, nutritional beverages, mayonnaise, sour cream, ice cream, yogurt, salad dressing and other foods and beverages that need to be opacified. The opacifying agent can also be incorporated into non-food formulation, such as cosmetics, creams and lotions.

36 Claims, 2 Drawing Sheets

STARCH-BASED OPACIFYING AGENT FOR FOODS AND BEVERAGES

RELATED APPLICATION

This is a continuation-in-part of U.S. patent application Ser. No. 08/221,178, filed Mar. 31, 1994, now abandoned. The entire teachings of this application is incorporated herein by reference.

BACKGROUND

Titanium dioxide ($TiO_2$) is a white pigment that is readily used in the food, drug and cosmetic industries. Titanium dioxide is stable and has demonstrated nontoxicity. It has been permanently listed by the Food and Drug Administration in 1963 as safe for human ingestion in foods, drugs and cosmetics. Use of titanium dioxide, however, is restricted to one percent by weight in food. Titanium dioxide has been similarly approved in most countries of the world.

Titanium dioxide tends to precipitate in formulated food products especially in non-viscous food systems such as creamers because of its insolubility and high density. Another disadvantage is that titanium dioxide can be deposited onto processing equipment and storage containers. This makes clean up of the titanium dioxide residue problematic and may also interfere with processing machinery.

SUMMARY OF THE INVENTION

The present invention pertains to a starch-based opacifying agent, to methods of manufacture and to food and non-food formulations containing the starch-based opacifying agent. The preferred starch-based opacifying agent will comprise a complex of starch and an opacifying agent such as titanium dioxide or other aqueous insoluble inorganic or organic compounds. Preferably the starch will be in the form of a partially hydrolyzed, pregelatinized starch. The invention also pertains to low fat and fat-free foods and beverages containing the starch-based opacifying agent, such as coffee creamer, cottage cheese dressing, nutritional beverages, mayonnaise, sour cream, ice cream, yogurt, salad dressing and other foods and beverages which need to be opacified. The opacifying agent can also be incorporated into non-food formulations including but not limited to cosmetics, creams, lotions, drugs, plastics, paints, shellacs, varnishes, inks, paper and textiles.

In a preferred embodiment, the starch-based opacifying agent comprising titanium dioxide as the opacifier is formulated into a low fat or fat free creamer, in either liquid or dry forms. The creamer is stable over storage and does not flocculate or feather when added to coffee, for example, or other beverage. The creamer can be opacified to the extent that it resembles a full fat creamer.

The starch-based opacifying agent has a number of advantages. It has a superior white pigmentation due to the presence of titanium dioxide or other opacifier, while the presence of starch stabilizes the titanium dioxide or other opacifier within the complex. In one embodiment, the stabilized form of titanium dioxide will substantially inhibit the deposition of titanium dioxide onto processing equipment and storage containers. This will facilitate clean up of processing equipment and will prevent damage to the equipment due to excessive build up of titanium dioxide, if the novel titanium dioxide-starch complex is used. Use of calcium salts as the opacifier provides the additional benefit of calcium fortification.

DETAILED DESCRIPTION OF THE INVENTION

Figure 1:
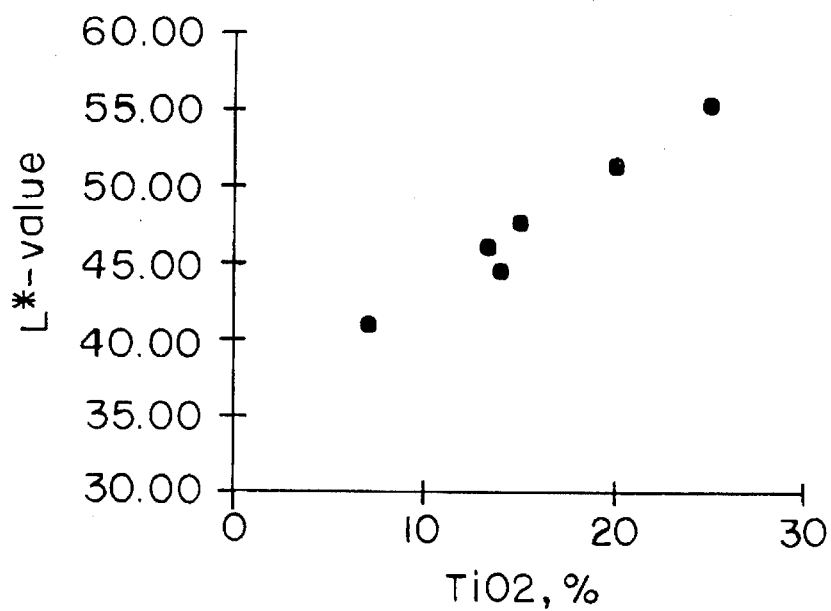
FIG. 1 is a graph showing the L*-value of coffee with coffee creamer as a function of titanium dioxide concentration in the novel starch-based opacifying agent.

The invention pertains to a novel starch-based opacifying agent, to methods for producing the starch-based opacifying agent, and to food, beverage and non-food formulations containing the starch-based opacifying agent. The starch-based opacifying agent comprises an opacifier and starch in the form of a complex in which the opacifier has been stabilized or entrapped therein.

The term "complex" is intended herein to mean an intimately associated relationship between the starch network and particles of the opacifier. For example, titanium dioxide particles are incorporated into and become part of the starch matrix, as seen by scanning electron microscopy.

The complex will comprise an opacifying agent which is an aqueous insoluble inorganic or organic compound having low particle size (e.g., less than one micron) and having proper refractive index to provide opacity. Compounds having these properties can be readily determined by one skilled in the art. Examples of suitable opacifiers include but are not limited to titanium dioxide, calcium salts, sodium salts, magnesium salts and barium salts (citrates, carbonates, sulfates, oxides). Aqueous insoluble proteins such as whey protein or prolamines can also be used as opacifying agents. Titanium dioxide is the preferred opacifying agent.

The opacifying agent can be incorporated into a starch matrix under specific conditions during processing of the starch. The amount of opacifier depends upon the desired food or cosmetic formulation and the degree of opacity desired. The preferred amount of opacifying agent will be from about 5 to about 50 percent by weight, with 15 percent being most preferred for titanium dioxide. The terms "opacity" and "opacifying power" refer to the amount of light reflectance of a suspension. As the dispersion becomes cloudy, the opacity increases and the amount of light reflected increases. The dispersion may be in liquid, solid or semi-solid form.

The starch component will preferably be in the form of partially hydrolyzed, pregelatinized starch. Processes for making such starch have been described in detail in PCT/US94/11654, filed Oct. 14, 1994, and U.S. patent application Ser. No. 08/138,541, filed Oct. 15, 1993, which is a continuation-in-part of U.S. Ser. No. 07/900,899, filed Jun. 13, 1992, to Francis M. Mallee and Eugene Terry Finocchiaro. The teachings of these applications are incorporated herein by reference in their entirety.

According to the method of this invention, starch-based opacifying agents are prepared from a high amylose starch which contains greater than about 30% amylose, and preferably about 70% amylose as determined by the iodine binding method. The high amylose starch can be obtained from a variety of plant sources, including but not limited to peas, oats, corn and barley. In addition, the high amylose starch can be chemically modified, for example by succinylation or crosslinking using known techniques. The starting material may be a product of the milling of whole grains in which the non-starch components of the grain have been removed. The milled starch product may be obtained in a wet or dry form. A number of commercial sources of high amylose starch include AMYLOMAIZE® VII (approx. 70% amylose; American Maize Products Co., Hammond, Ind.) and HYLON® VII (National Starch and Chemicals Co., Bridgewater, N.J.).

The method for producing the novel starch-based opacifying agents generally involves: cooking the slurry under conditions of time, temperature, pressure, pH, ionic strength and shear sufficient to solubilize the starch by fully disrupting the starch granules while minimizing generation of objectionable side products which contribute off-flavor and off-color; filtering the solubilized starch to remove a substantial portion of non-starch components such as lipid and protein, preferably by treatment with diatomaceous earth and activated charcoal; adding an opacifier under controlled conditions of temperature and shear; optionally homogenizing the filtrate; and cooling of the fully solubilized starch under controlled conditions of time, temperature and shear to yield a thixotropic gel. The retrograded starch-based opacifying agent can be dried to reduce the moisture content to provide a free-flowing powder. Alternatively, the filtered starch solution can be dried at a temperature sufficient to maintain the solubility of the starch to yield a powdered non-crystalline, non-retrograded, amorphous product that is more readily hydrated in water than retrograded starches. A third alternative is to cool the filtered starch solution to a temperature and for a period of time sufficient to allow partial precipitation of the starch, thereby resulting in a partially retrograded starch-based opacifying agent. In any of these three cases, the starch-based opacifying agents can be used directly in food formulations. The dry powder may be used directly or can be rehydrated prior to use. Each of these steps are discussed in detail below.

Specifically, the method involves preparing a starch slurry in an aqueous medium with a total high amylose starch content of from about 1 to about 30% (w/w) solids, preferably from about 5 to about 15% (w/w). For purposes of the present invention, "aqueous medium" is defined as water or a solution which is substantially water such as buffer, acid, base, salt, antioxidant, reducing agent, and/or chelating agent solutions or a blend of water with a miscible organic solvent, in an amount sufficient to inhibit oxidation of lipids present in the starch starting materials. It is preferred that the aqueous medium, such as water, be pretreated to remove any dissolved minerals. The starch may be hydrated at ambient temperature or after the aqueous medium has been heated.

The resulting slurry is transferred into an evacuated reactor vessel equipped with appropriate stirring device for agitation during the cooking of the starch slurry. The starch slurry is subjected to controlled conditions of time, temperature, pressure, pH, ionic strength and shear, to fully disrupt the starch granules and solubilize the starch. For the purposes of the present invention, the term "solubilize" refers to the absence of any detectable particulate matter, especially partially disrupted starch granules, when viewed under 200 to 400-fold magnification using a standard light microscope. The rate of heating, time duration at the final cook temperature (i.e., the temperature above the gelatinization temperature of starch), and shear rate in the reactor vessel affect the properties of the final product.

The slurry is typically heated from room temperature (approximately 22° C.) to from about 125° C. to about 150° C., with about 138° C. being preferred, under stirring over a time period which ranges from 40 to 120 minutes, preferably 60 minutes until starch granules are solubilized. Variations in initial temperature and rate of heating affect the properties of the final product even though the total time at 138° C. is essentially unchanged. These times are representative for batch cooking and will differ if jet cooking is used, as discussed below.

The final temperature of 138° C. for cooking of the starch is preferred to produce products that possess smooth mouth-feel, high opacity, and acceptable organoleptic properties. The complete disruption and solubilization of the starch is monitored by periodic sampling of small aliquots from the reactor over time and examination of the slurry under magnification (e.g., 200 to 400×) for presence or absence of starch granules. The heating step is considered complete when essentially all the starch granules have dissolved. The importance of the final temperature used in the present invention is illustrated by the following comparison. High amylose starch was heated to a maximum temperature in the reactor of 121° C. for 8 hours in the absence of shear. Even though the cooking process is carried out for a much longer time period than that of the present invention, this lower temperature does not allow for complete solubilization and disruption of the starch granules resulting in a product that contains relatively large particulates that exhibit grittiness and poor mouth-feel when tasted directly. In contrast, the higher temperature used in the present process insures full disruption of the starch granules and solubilization of the high amylose starch which yields a much smoother product.

Removal of oxygen from the slurry is important to produce a product with minimal off-color and off-flavor, as ascertained by visual and sensory perception. It is preferred that the dissolved oxygen content be less than 1 ppm to ensure that off-flavors resulting from oxidation are not perceived upon tasting. For example, this can be achieved by subjecting the slurry to a vacuum, sparging with an inert gas such as argon or nitrogen using either a vented vessel or closed vessel, or any combination of techniques effective for removal of dissolved gases especially oxygen from the slurry, such as oxygen scavengers. Deaerating can be carried out for a period of time necessary to insure removal of the bulk of the dissolved gases typically up to one hour, preferably, ten minutes. Other approaches to reduce off-flavors and off-colors may include, either alone or in combination, near complete removal of non-starch components from the starting material, the addition of antioxidants, reducing agents and or chelating agents to the slurry, or washing of the final product with aqueous or organic solvents, among other generally known methods.

An alternative method of heating is to directly inject steam into the slurry, such as can be accomplished in a rapid heat-up device such as a jet cooker. Using a jet cooker or other rapid heat-up device, higher temperatures above the preferred range can be tolerated without affecting product properties if the contact time is sufficiently short. Generally, the temperature is raised up to about 160° C. and maintained at the elevated temperature for up to about ten minutes. Higher temperatures can be used for shorter time periods.

According to the methods of this invention, the typical pH of the slurry before and after cooking is in the range from about 3.0 to about 7.0. However, the pH at which the starch is cooked will be dictated by the end product containing the starch-based opacifying agent. For beverages, such as coffee and milk, the pH should be more acidic, i.e., from about 3.0 to about 4.7. It has been shown herein that lower pH results in more extensive hydrolysis of the complex, and enhances the stability of the complex when used in coffee. If adequate hydrolysis does not occur, then the complex will flocculate or feather when added to coffee, for example. For other food formulations such as cottage cheese, it is not necessary to hydrolyze the complex to the degree needed for a titanium dioxide-starch complex that is used in beverages. The pH is preferably from about 4.3 to about 4.7. The method of cooking will also dictate the pH at which the starch is cooked. If a jet cooker is used, the pH should be lower than for batch cooking.

Regulation of pH further effects the dextrose equivalent (DE). The lower the pH of the slurry, the greater the degree of hydrolysis and thus a high DE value. The preferred range for dextrose equivalent is from about 2.5 to about 6, with from about 4 to about 5 for creamers, and from about 2 to about 3 for other food formulations (e.g., cottage cheese dressing).

Upon complete disruption of the starch granules and solubilization of the starch, the starch solution is cooled to a temperature below boiling and above about 85° C., with 100° C. being preferred. Temperatures lower than about 85° C. will result in inefficient filtration as the starch retrogrades. Cooling can be accomplished by any suitable means such as flash cooling, heat exchangers and by running cooling water through the reactor jacket. The cooled starch solution is then transferred from the reactor vessel by expulsion under pressure, pumping, or other suitable method.

The starch solution (at approximately 90° C.) is filtered to remove undissolved impurities, such as protein, fats and other compounds. Any filtration device having metal sieves, filter papers/cloths, filter pads or other filter media can be used. For example, plate and frame filter presses, cartridges, ceramic filters and membranes, bag and pressure leaf filters can be used. It is desirable to preheat the filters and filtering device to the temperature of the slurry to be filtered prior to filtration. This will prevent premature retrogradation of the starch on the filter media and consequent blinding of the filter.

The filtration step is preferably performed by filtering the solution through a secondary carbon-containing filter such as a filter fitted with activated charcoal impregnated pads or a filter fitted with a cartridge containing activated charcoal. In a preferred embodiment, a filter aid such as diatomaceous earth is typically added to the starch solution and stirred for about ten to about 120 minutes, with 60 minutes being preferred. The amount of diatomaceous earth used is generally from about 5% to about 20% by weight of the starch being purified, and is preferably about 10% by weight. The starch solution is then passed through a primary filter to remove the diatomaceous earth and then through the secondary filter containing the activated charcoal impregnated pads. Suitable carbon impregnated pads are available, for example, from Alsop Engineering Co., Kingston, N.Y. (S-51, grade 872).

Alternatively, the filtration step is performed by treating the starch solution with activated charcoal. Activated charcoal is added to the reactor vessel for approximately from about 10 to about 120 minutes, with 60 minutes being preferred. Typically, the solution is simultaneously treated with a filtering aid such as diatomaceous earth, e.g. CELETE® (CELITE® Corp.). The amount of diatomaceous earth generally used is as described above. The starch solution containing suspended activated charcoal and diatomaceous earth is then filtered, as described above, to remove the charcoal and diatomaceous earth.

Starch-based opacifying agents which have been treated with activated charcoal and diatomaceous earth have reduced protein and fat contents compared with starch-based opacifying agents which have not undergone this treatment. By removing impurities from the starch solution which prevent retrogradation, filtration facilitates the retrogradation of the starch. In addition, treatment with diatomaceous earth and activated charcoal gives the resulting starch-based opacifying agent improved sensory properties such as flavor.

The filtered starch solution is collected in a receiving vessel. A retrograded, non-retrograded or partially retrograded starch can be produced from the filtered starch solution, depending on how the solution is processed. Drying the filtered starch solution before the starch precipitates produces a non-retrograded starch. Allowing the solution to cool so that the starch precipitates yields a retrograded starch. Adjusting the temperature and time of precipitation so that the starch only partially precipitates results in a partially retrograded starch.

A retrograded starch is produced by cooling the filtered or treated starch solution to a temperature sufficient to allow the starch to precipitate, typically from about 1° C. to 7° C., preferably to about 4° C. Optionally, salts suitable for use in food such as sodium chloride can be added to increase the rate of crystallization.

Optionally, the treated, filtered starch solution can be subjected to shear before being allowed to retrograde in order to improve the sensory properties of the product. Shear may be provided by piston, probe, jet, or valve homogenization (e.g., one and two stage), colloid milling, or similar technique. Conditions of shear will vary with the specific technique employed.

Titanium dioxide or other opacifier is added to the filtered starch solution at a temperature of from about 75° C. to about 95° C. under agitating conditions. The amount of titanium dioxide or other opacifier will depend upon the degree of opacity desired as discussed above. The resulting mixture is allowed to cool under mild agitation until the viscosity increases and gelation is initiated. Typically the temperature at which this occurs is from about 40° C. to about 50° C. It is desirable to agitate the mixture during cooling to keep the titanium dioxide from sedimenting. Agitation will also ensure uniform distribution of the titanium dioxide or other opacifier through out the starch complex.

Once removed from the vessel, the gel is allowed to cool to a temperature to fully gel the starch complex. The preferred temperature is about 4° C. Cooling should be carried out with a minimum of shear for maximum gel strength in the resultant gel; however, application of shear during the cooling step can be used to produce material with varied functional properties, i.e., lower viscosity. For example, the homogenate can be stored in a temperature controlled cooler overnight. After completion of the cooling process, the resultant paste-like gel can be stored in the temperature range of from about 4° C. to about 50° C., preferably about 4° to about 22° C.

The product, in the form of a paste, can then be used directly in food or cosmetic formulations or dried by an appropriate method to a white, free-flowing powder. If the gel is dried, the preferred method is to use a spray dryer to achieve rapid drying. This preserves the functional characteristics and facilitates rehydration. Any drying method known to those skilled in the art can be used. For example centrifugal atomizers, pressure nozzles and two fluid nozzles can be used to atomize the starch gel. Alternative drying methods can be used and include drum drying and freeze drying.

The properties of the starch-based opacifying agent may be further modified by adding excipients such as sugars, maltodextrin that aid in hydration, other starches, and/or other components such as proteins, flavors, colors, lipids, etc. Preferred excipients are any hydrolyzed starch-based carbohydrate, with low DE maltodextrin being most preferred. Excipients that aid in rehydration are not necessary if the resultant starch solution is used in wet form without prior drying and rehydration or if the dry powder is rehydrated under conditions of sufficient heat and shear to insure complete rehydration.

In another embodiment, the process described above can be modified so that the cooked starch/opacifier complex is spray dried prior to gelation. Spray drying can be performed immediately after the cooking step or after the starch has been cooled to a temperature from between about 45° C. and about 95° C., prior to gelation. The opacifying agent is added to the filtered starch solution (as described above) at about 75° C. to 95° C. and stirred under high shear. At this temperature, the resulting solution is fed to a spray drier, with the inlet temperature being set at from about 170° C. to about 200° C. and the outlet temperature being set at from about 90° C. to about 120° C. If an excipient or other additive is used, it can be added prior to or after the addition of the opacifier. Preferably, maltodextrin as excipient will be added to the cooked starch prior to filtration and addition of the opacifier.

The microstructure of the product as characterized by SEM can be described as a semi-continuous, gel network which is devoid of starch granules or granule fragments. The discontinuous portions of the network appear as irregularly-shaped microparticles. The titanium dioxide particles are intimately incorporated into the starch matrix, with little, if any evidence of free titanium dioxide particles.

The starch-based opacifying agents of this invention are versatile and function in full-fat foods or can fully or partially replace fat in a variety of food products which typically contain a high percentage of fat in their formulation. Generally, the starch-based opacifying agents can be incorporated into food formulations at levels between about 0.1 and about 10%, preferably between about 0.5 and about 6% (w/v). Suitable foods and beverages that can be formulated include coffee creamer, cottage cheese dressing, nutritional beverages, mayonnaise, sour cream, ice cream, yogurt, salad dressing and other foods and beverages that require opacification. The fat-like attributes and stability are achieved without chemical modification of the starch. As a result of these fat-like attributes and opacity, food formulations normally containing fat can now be made having reduced levels of fat approaching 100% reduction in certain formulations but still have the opacity of a full fat equivalent. The stability of the starch-based opacifying agent in food depends upon the pH and temperature of the food. For example, a creamer containing the starch/titanium dioxide complex is stable in cold water or tea but tends to be more unstable in low pH/high temperature food systems such as hot coffee where the creamer containing the complex is stable therein for approximately 30 minutes.

In a preferred embodiment, a starch-based opacifying agent containing AMYLOMAIZE VII® starch and titanium dioxide as the opacifier can be formulated into a creamer that is suitable for use in coffee or other beverages. Due to the whitening power of the titanium dioxide and the inherent texturizing properties of the starch, fat free and low fat creamers that resemble full fat creamers, in terms of organoleptic properties and appearance, can be made. As shown in the examples, a low fat creamer was prepared and its performance in coffee was evaluated against a commercially available half-n-half creamer and non-fat creamer products. The low fat creamer containing the starch-based opacifying agent had a viscosity and whitening power comparative to half-n-half. The creamer was stable over storage and freeze/thaw and exhibited good resuspendability. Further, the creamer did not exhibit any signs of flocculation for at least 30 minutes in hot coffee.

In a comparative study, titanium dioxide/starch complex and an admixture of pregelatinized starch and titanium dioxide were evaluated for their stability and texturizing properties. The complex when added to a creamer is superior in stability relative to the starch/titanium dioxide admixture. In cottage cheese for example, the textural properties were superior when the complex was added compared to similar product containing the starch/titanium dioxide admixture. Thus, the intimate association of the titanium dioxide in the starch matrix provides enhanced properties of the product. These properties are not observed with simple admixtures of similar ingredients.

The starch-based opacifying agent can be incorporated into non-food formulations such as cosmetics, creams, lotions (e.g., suntan lotion), drugs, plastics, paints, shellacs, varnishes, inks, paper and textiles.

The novel products of this invention function to provide structure, opacity, viscosity, stability, and acceptable organoleptic attributes with performance approximating the qualities of the full fat versions when used in reduced fat or fat-free foods and beverages. The starch-based opacifying agents lack off-flavors, and do not mask the inherent flavors when added to a food formulation. The food formulations containing the opacifying agents of the present invention exhibit excellent freeze/thaw and frozen storage stability, shelf stability and resistance to shear. The stabilized form of titanium dioxide will substantially inhibit the deposition of titanium dioxide onto processing equipment and storage containers. This will facilitate clean up of processing equipment and will prevent damage to the equipment due to excessive build up of titanium dioxide, if the novel titanium dioxide-starch complex is used. The opacifying agents of the present invention have been shown to function well with both laboratory and commercial plant processing schemes and equipment. Use of calcium salts as the opacifier provides the additional benefit of calcium fortification.

The invention will be further illustrated by the following examples which are not to be construed as limiting in any way. All weights and percentages are given below as weight/weight unless otherwise specified.

EXAMPLES

Example 1

Small Scale Production of Starch-based Opacifying Agent (High DE, High $TiO_2$ Complex)

Five hundred and fifty grams of 70% amylose corn starch (AMYLOMAIZE VII starch®, American Maize Products Co., Hammond, Ind.) was weighed into an 8 quart stainless steel beaker. Five thousand two hundred and four grams of deionized water was added to the beaker. The final starch solids concentration was 9.6% (w/w). The starch suspension was stirred using a LIGHTNIN™ Mixer (Lightnin Mixers, Rochester, N.Y., Model #TS1515) at 250 rpm. The pH of the suspension was checked and adjusted from 5.68 to 3.25 with 4.5 ml 1N HCl. The suspension was then transferred to a two gallon Parr reactor (Parr Instrument Co., Moline, Ill., Model No. 4552) by pulling a vacuum inside the reactor and drawing the suspension through an inlet port. While stirring at 360 rpm, the batch was sparged with nitrogen gas for 10 minutes. The batch was then heated from 20° C. to 138° C. in 79 minutes. After holding the batch temperature at 138° C. for 26 minutes, 10 ml of the batch was removed from the reactor by opening an outlet port. The sample was examined for the presence of remaining starch granules or granule fragments with a microscope (Olympus Corporation, Lake Success, N.Y., Model BHS) under 200-fold magnification. Because no granule fragments were observed, the batch was cooled to 100° C. in 20 minutes. The reactor was then pressurized to 30 psi with nitrogen gas and discharged through a 12 inch round plate and frame filter press (Alsop Engineering, Kingston, N.Y., Model ST120B4) fitted with two carbon filters (Grade 872, Alsop Engineering, Kingston, N.Y.). The batch was collected in an 8 quart stainless steel beaker and stirred at 250 rpm. Ninety nine grams of maltodextrin (MALTRIN® M040, Grain Processing Corporation, Muscatine, Iowa) was added to the batch and stirred until completely dissolved. The batch was then split into two equal portions of 1550 grams each and transferred to two 4 liter beakers. Twelve and a quarter grams titanium dioxide powder (Warner Jenkinson, St. Louis, Mo., KOWET™) was added to one beaker and 28.75 grams titanium dioxide powder to the other beaker at approximately 75°–85° C. The beakers were stirred at 250 rpm with LIGHTNIN™ Mixers until the contents had cooled to approximately 40°–50° C. to set a partial gel and prevent the titanium dioxide from sedimenting. The beakers were then removed from agitation and allowed to cool overnight at 4° C. Each beaker of material was fed to a spray-drier (Niro Atomizer, Copenhagen, Denmark, Model #1291) fitted with a centrifugal atomizer. Inlet air temperature was regulated to maintain outlet air temperature at 125° C. The DE value of the product was 3.3.

Example 2

Pilot Scale Preparation of Starch-based Opacifying Agent (High DE, High $TiO_2$ Complex)
Method 1: Quiescently Cooled Two hundred pounds of reverse-osmosis deionized (RODI) water was metered into a 30 gallon (114 liter) reactor (Lee Kettles, Phillipsburg, N.J.) and heated to 46.7° C. Twenty five pounds (11.3 kilograms) of 70% amylose corn starch (AMYLOMAIZE VII® starch, American Maize Products Co., Hammond, Ill.) was weighed into the reactor. The final starch solids concentration was 10% (w/w). The reactor contents were agitated at 340 rpm using a LIGHTNIN™ Mixer (Lightnin Mixers, Rochester, N.Y.; Model V5S18 with an A-310 impeller). The pH of the suspension was adjusted to 3.45 using 15% phosphoric acid. The batch was heated from 46.0° C. to 105° C. in 15 minutes. The heating began with the vessel open to atmospheric pressure. The vessel was sealed by closing a vent valve when the product temperature reached 97° C. The temperature was then raised from 105° C. to 138° C. in 60 minutes. The product was held at 138° C. for 60 minutes. The product was then cooled from 138° C. to 95° C. in 9 minutes by circulating 45° C. chilled water through the reactor jacket. The product was maintained at 95° C. by again adding steam to the jacket and the reactor was open. Seven and a half pounds (3.40 kilograms) of maltodextrin (MALTRIN® M040, Grain Processing Corp., Muscatine, Iowa) and 2.5 pounds (1.13 kilograms) of diatomaceous earth (CELITE®, CELITE® Corporation, Lompoc, Calif.) were added. The batch was held for 60 minutes before filtering through two filter presses, in series. The first press (Model BT-240, Alsop Engineering Co., Kingston, N.Y.) was dressed with four 24" (61.0 cm) square filter pads (A-10 pads, Alsop Engineering Co.). The press had one 2-inch (5.08 cm) wide frame installed between two one-half inch (1.27 cm) wide filter plates. The second press (Alsop Engineering Co.) was dressed with three 13 inch (33.0 cm) square carbon filter pads (1640HC pads, Cellulo Corporation, Fresno, Calif.) The presses had been preheated by circulating 95° C. RODI water through them. The batch was pumped at 15.9 lbs/minutes (7.21 kg/min) through the filter presses and into a holding kettle. Titanium dioxide powder (KOWET™, Warner Jenkinson, St. Louis, Mo.) was added to the starch-maltodextrin solution and mixed for 5 minutes in a high shear mixer (Likwifier, Breddo, Inc., Kansas City, Kans.) at approximately 75°–85° C. The solids content of the product was 15% titanium dioxide and 85% starch maltodextrin. The product was then emptied from the mixer into five-gallon (18.9 liter) pails and placed in a 4° C. refrigerator over-night. The product was removed from the refrigerator 30 hours later and was spray-dried. The spray dryer (APV Crepaco, Tonawanda, N.Y.) inlet and exit air temperatures were 218° C. and 104° C. respectively. The DE value of the product was 5.1.

Example 3

Pilot Scale Preparation of Starch-based Opacifying Agent (High DE, High $TiO_2$ Complex)
Method 2: Spray Dried Without Prior Gelation Six hundred and seventy lbs (304 kg) of reverse-osmosis, deionized (RODI) water was metered into a 100 gallon (379 liter) reactor (Lee Kettles, Phillipsburg, N.J.) and heated to 43.6° C. Eighty four lbs (38.1 kg) of 70% amylose corn starch (AMYLOMAIZE VII®, American Maize Products Co., Hammond, Ill.) was weighed into the reactor. The final starch solids concentration was 10% (w/w). The reactor contents were agitated using a LIGHTNIN™ mixer (Lightnin Mixers, Rochester, N.Y.) Model V5S18 with an A-310 impeller at 340 rpm. The pH of the suspension was adjusted to 3.75 by adding 15% phosphoric acid. The batch was heated from 43.6° C. to 105° C. in 14 minutes. The heating began with the vessel open to atmospheric pressure. The vessel was sealed by closing a vent valve when the product temperature reached 97° C. The temperature was then raised from 105° C. to 138° C. in 60 min. The product was held at 138° C. for 62 min. The product was then cooled from 138° C. to 94.4° C. in 12 minutes by circulating 7° C. chilled water through the reactor jacket. The product was maintained at 95° C. by again adding steam to the jacket and the reactor was opened. Twenty five lbs (11.3 kg) of maltodextrin (MALTRIN® M040, Grain Processing Corp, Muscatine, Iowa) and 8.4 lbs (3.81 kg) of diatomaceous earth (CELITE®, CELITE® Corporation, Lompoc, Calif.) were added. The batch was held for 60 minutes before filtering through two filter presses in series. The first press (Model BT-240, Alsop Engineering Co., Kingston, N.Y.) was dressed with six 24" (61.0 cm) square filter pads (A-10 filter media, Alsop Engineering Co.). The press had one 2-inch (5.08 cm) wide frame installed between two one-half inch (1.27 cm) wide filter plates. The second press (Alsop Engineering Co.) was dressed with five 13-inch (33.0 cm) square carbon filter pads (1640HC pads, Cellulo Corporation, Fresno, Calif.). The presses had been preheated by circulating 95° C. RODI water through them. The batch was pumped into a 14.9 lbs/min (6.78 kg/min) through the filter presses and into a holding kettle. Titanium dioxide powder (KOWET™, Warner Jenkinson, St. Louis, Mo.) was added to the starch-maltodextrin solution and mixed in a high shear mixer (Likwifier, Breddo, Inc., Kansas City, Kans.). The solids content of the product was 15% titanium dioxide and 85% starch-maltodextrin. The product was fed to the spray dryer at about 95° C. The spray dryer (APV Crepaco, Tonawanda, N.Y.) inlet and exit air temperatures were 160° C. and 100° C., respectively. The DE value of the product was 4.5.

Example 4

Pilot Scale Preparation of Starch-based Opacifying Agent (Low DE, Low $TiO_2$ Complex)

Eight hundred lbs (363 kg) of reverse-osmosis, deionized (RODI) water was metered into a 30 gallon (114 liter) reactor (Lee Kettles, Phillipsburg, N.J.) and heated to 46.7° C. One hundred lb (45.4 kg) of 70% amylose corn starch (AMYLOMAIZE VII®, American Maize Products Co., Hammond, Ill.) was weighed into the reactor. The final starch solids concentration was 10% (w/w). The reactor contents were agitated using a LIGHTNIN™ mixer (Lightnin Mixers, Rochester, N.Y.) Model V5S18 with an A-310 impeller at 340 rpm. The pH of the suspension was adjusted to 4.48 using 15% phosphoric acid. The batch was heated from 45.3° C. to 105° C. in 16 minutes. The heating began with the vessel open to atmospheric pressure. The vessel was sealed by closing a vent valve when the product temperature reached 97° C. The temperature was then raised from 105° C. to 138° C. in 60 minutes. The product was held at 138° C. for 60 minutes. The product was then cooled from 138° C. to 95° C. in 15 minutes by circulating 7° C. chilled water through the reactor jacket. The product was maintained at 95° C. by again adding steam to the jacket and the reactor was opened. Ten lbs (4.54 kg) of diatomaceous earth (CELITE®, CELITE® Corporation, Lompoc, Calif.) and 30.3 lbs (13.7 kg) of maltodextrin (MALTRIN® M040, Grain Processing Corp., Muscatine, Iowa) were added. The batch was held for 60 minutes before filtering through two filter presses in series. The first press (Model BT-240, Alsop Engineering Co., Kingston, N.Y.) was dressed with six 24" (61.0 cm) square filter pads (A-10 filter media, Alsop Engineering Co.). The press had one 2-inch (5.08 cm) wide frame and one half inch (127 cm) frame installed between one-half inch (127 cm) wide filter plates. The second press (Alsop Engineering Co. was dressed with five 13 inch (33.0 cm) square carbon filter pads (1640 HC pads, Cellulo Corporation, Fresno, Calif.). The presses had been preheated by circulating 95° C. RODI water through them. The batch was pumped at 31.9 lbs/min (14.5 kg/min) through the filter presses and into a holding kettle. Titanium dioxide (Warner Jenkinson, St. Louis, Mo.) was added to the starch-maltodextrin solution and mixed for 5 minutes in a high shear mixer (Likwifier, Breddo Inc., Kansas City, Kans.). The product solids were 7% titanium dioxide and 93% starch-maltodextrin. The product was then emptied from the mixer into five-gallon (18.9 liter) pails and placed in a 4° C. refrigerator. The product was removed from the refrigerator 16 hours later and spray dried. The spray dryer (APV Crepaco, Tonawanda, N.Y.) inlet and exit air temperature were 195° C. and 108° C., respectively. The DE value of the product was 2.5.

Example 5

Pilot Scale Production of Starch-based Opacifying Agent with AMYLOMAIZE VII® Starch Without Maltodextrin Six hundred and seventy lbs (304 kg) of reverse-osmosis, deionized (RODI) water was metered into a 100 gallon (379 liter) reactor (Lee Kettles, Phillipsburg, N.J.) and heated to 44.5° C. Eighty four lbs (38.1 kg) 70% amylose corn starch (AMYLOMAIZE® VII, American Maize Products Co., Hammond, Ill.) was weighed into the reactor. The final starch solids concentration was 10% (w/w). The reactor contents were agitated using a LIGHTNIN™ mixer (Model V5S18, Lightnin Mixers, Rochester, N.Y.) with an A-310 impeller at 340 rpm. The pH of the suspension was adjusted to 4.05 by adding 15% phosphoric acid. The batch was heated from 44.5° C. to 105° C. in 15 minutes. The heating began with the vessel open to atmospheric pressure. The vessel was sealed by closing a vent valve when the product temperature reached 97° C. The temperature was then raised from 105° C. to 138° C. in 45 minutes. The product was held at 138° C. for 60 minutes. The product was then cooled from 138° C. to 95° C. in 12 minutes by circulating 7° C. chilled water through the reactor jacket. The product was maintained at 95° C. by again adding steam to the jacket and the reactor was opened. Eight and a half lbs (3.81 kg) of diatomaceous earth (CELITE®, CELITE® Corporation, Lompoc, Calif.) was added and the product was held for 30 minutes. After 30 minutes, a portion of the batch was filtered through a 12" (30.5 cm) diameter filter press (Model ST120B-4, Alsop Engineering Co., Kingston, N.Y.) dressed with six filter pads (230 filter media, Alsop Engineering Co.) and 35.4 lbs (16.1 kg) of starch solution was collected. 0.67 lbs (0.309 gm) of titanium dioxide (KOWET™ Warner Jenkinson, St. Louis, Mo.) was added The product was mixed in a high shear mixer, Likwifier, Breddo, Inc., Kansas City, Kans.) and poured into 5 gallon (18.9 liter) pails, and refrigerated at 4° C. overnight and subsequently spray dried. The spray dryer (APV Crepaco, Tonawanda, N.Y.) inlet and exit air temperature were 195° C. and 108° C., respectively. The DE value of the product was 1.27.

Example 6

Small Scale Production of Starch-based Opacifying Agent with AMYLOMAIZE V® Without Maltodextrin Five hundred and fifty grams of 50% amylose corn starch (AMYLOMAIZE V®, American Maize Products Co., Hammond, Ind.) was weighed into an 8 quart stainless steal beaker. Five thousand two hundred and four grams of deionized water was added to the beaker. The final starch solids concentration was 9.6% (w/w). The starch suspension was stirred using a LIGHTNIN™ Mixer (Lightnin Mixers, Rochester, N.Y., Model TS1515) at 250 rpm. The pH of the suspension was measured and adjusted from 5.65 to 3.82 with 15 ml 15% phosphoric acid. The suspension was then transferred to a two gallon Parr reactor (Parr Instruments Co., Moline, Ill., Model No. 4552) by drawing the suspension through the inlet port. The batch was stirred at a speed of 360 rpm while heating from 20° C. to 138° C. in 115 minutes. After holding the batch temperature at 138° C. for 26 minutes, 10 ml of the batch was removed from the reactor by opening the outlet port. The sample was examined for the presence of remaining starch granules or granule fragments with a microscope (Olympus Corp., Lake Success, N.Y., Model BHS) under 200-fold magnification. Since no granule fractions were observed, the batch was cooled to 100° C. in 30 minutes. The reactor was then pressurized to 30 psi with nitrogen gas and discharged through a 12 inch round plate and frame filter press (Alsop Engineering Co., Kingston, N.Y., Model ST120B4) fitted with two carbon filters (Grade 872, Alsop Engineering Co., Kingston, N.Y.). The batch was collected in an 8 quart stainless steel beaker and stirred at 250 rpm. The batch was then split into two equal portions of 1550 gram each and transferred to two 4 L beakers. One beaker which contained a control for the run without titanium dioxide was then allowed to cool overnight at 4° C. Twenty three gram of titanium dioxide powder (Warner Jenkinson, St. Louis, Mo., KOWET™) was added to the other beaker at approximately 75°–85° C. The beaker was stirred at 250 rpm with Lightnin Mixer until the contents had cooled to approximately 40°–50° C. The beaker was then removed from agitation and allowed to cool overnight at 4° C. Each beaker of material was fed into the spray-drier (Niro Atomizer, Copenhagen, Denmark, Model #1291) fitted with a centrifugal atomizer. Inlet air temperature was regulated to maintain outlet air temperature at 125° C. The DE value of the product was 1.24.

Example 7

Pilot Scale Preparation of Starch-based Opacifying Agent (High DE, Calcium Citrate Complex)

Six hundred and seventy lbs (304 kg) of reverse-osmosis, deionized (RODI) water was metered into a 100-gallon (379 liter) reactor (Lee Kettles, Phillipsburg, N.J.) and heated to 43.6° C. Eighty four lbs (38.1 kg) of 70% amylose corn starch (AMYLOMAIZE VII®, American Maize Products Co., Hammond, Ill.) was weighed into the reactor. The final starch solids concentration was 10% (w/w). The reactor contents were agitated using a LIGHTNIN™ mixer (Lightnin Mixers, Rochester, N.Y.) Model V5S18 with an A-310 impeller at 340 rpm. The pH of the suspension was adjusted to 3.75 by adding 15% phosphoric acid. The batch was heated from 43.6° C. to 105° C. in 14 minutes. The heating began with the vessel open to atmospheric pressure. The vessel was sealed by closing a vent valve when the product temperature reached 97° C. The temperature was then raised from 105° C. to 138° C. in 60 minutes. The product was held at 138° C. for 62 minutes. The product was then cooled from 138° C. to 94.4° C. in 12 minutes by circulating 7° C. chilled water through the reactor jacket. The product was maintained at 94.4° C. by again adding steam to the jacket and the reactor was opened. Twenty five lbs (11.34 kg) of maltodextrin (MALTRIN® M040, Grain Processing Corp., Muscatine, Iowa) and 8.4 lbs (3.81 kg) of diatomaceous earth (CELITE®, CELITE® Corporation, Lompoc, Calif.) were added. The batch was held for 77 minutes before filtering through two filter presses in series. The first press (Model BT-240, Alsop Engineering Co., Kingston, N.Y.) was dressed with six 24" (61.0 cm) square filter pads (A-10 filter media, Alsop Engineering Co.). The press had one 2-inch (5.08 cm) wide frame and one one-half inch wide frame installed between one-half inch (1.27 cm) wide filter plates. The second press (Alsop Engineering Co.) was dressed with five 13-inch (33.0 cm) square carbon filter pads (164OHC pads, Cellulo Corporation, Fresno, Calif.). The presses had been preheated by circulating 95° C. RODI water through them. The batch was pumped through the filter presses and into a holding kettle. Calcium citrate prepared according to U.S. Pat. No. 5,194,270 was added to the starch-maltodextrin solution and mixed for 5 minutes in a high shear mixer (Likwifier, Breddo, Inc., Kansas City, Kans.). The solids content of the product was 15% calcium citrate and 85% starch-maltodextrin. The product was then emptied from the mixer into five-gallon (18.9 liter) pails and placed in a 4° C. refrigerator. The product was removed from the refrigerator 30 hours later and spray dried. The spray dryer (APV Crepaco, Tonawanda, N.Y.) inlet and exit air temperatures were typically 195° C. and 125° C., respectively. The DE value of the product was 4.5.

Example 8

Pilot Scale Preparation of Starch-based Opacifying. Agent (High DE, Precipitated Calcium Carbonate Complex)

Six hundred and seventy lbs (304 kg) of reverse-osmosis, deionized (RODI) water was metered into a 100-gallon (379 liter) reactor (Lee Kettles, Phillipsburg, N.J.) and heated to 40.0° C. Eighty four lbs (38.1 kg) of 70% amylose corn starch (AMYLOMAIZE VII®, American Maize Products Co., Hammond, Ill.) was weighed into the reactor. The final starch solids concentration was 10% (w/w). The reactor contents were agitated using a LIGHTNIN™ mixer (Lightnin Mixers, Rochester, N.Y.) Model V5S18 with an A-310 impeller at 340 rpm. The pH of the suspension was adjusted to 3.88 by adding 15% phosphoric acid. The batch was heated from 40.0° C. to 105° C. in 14 minutes. The heating began with the vessel open to atmospheric pressure. The vessel was sealed by closing a vent valve when the product temperature reached 97° C. The temperature was then raised from 105° C. to 138° C in 44 minutes. The product was held at 138° C. for 60 minutes. The product was then cooled from 138° C. to 94.4° C. in 13 minutes by circulating 7° C. chilled water through the reactor jacket. The product was maintained at 94.4° C. by again adding steam to the jacket and the reactor was opened. Twenty five lbs (11.3 kg) of maltodextrin (MALTRIN® M040, Grain Processing Corp., Muscatine, Iowa) and 8.4 lbs (3.81 kg) of diatomaceous earth (CELITE®, CELITE® Corporation, Lompoc, Calif.) were added. The batch was held for 60 minutes before filtering through two filter presses in series. The first press (Model BT-240, Alsop Engineering Co., Kingston, N.Y.) was dressed with six 24" (61.0 cm) square filter pads (A-10 filter media, Alsop Engineering Co.). The press had one 2-inch (5.08 cm) wide frame and one one-half inch wide frame installed between one-half inch (1.27 cm) wide filter plates. The second press (Alsop Engineering Co.) was dressed with five 13-inch (33.0 cm) square carbon filter pads (164OHC pads, Cellulo Corporation, Fresno, Calif.). The presses had been preheated by circulating 95° C. RODI water through them. The batch was pumped through the filter presses and into a holding kettle. Precipitated calcium carbonate (USP Albaglos, Pfizer Specialty Minerals, Bethlehem, Pa.) was added to the starch-maltodextrin solution and mixed for 5 minutes in a high shear mixer (Likwifier, Breddo, Inc., Kansas City, Kans.). The solids content of the product was 15% calcium carbonate and 85% starch-maltodextrin. A portion of this product was then emptied from the mixer into five-gallon (18.9 liter) pails and placed in a 4° C. refrigerator. The product was removed from the refrigerator 30 hours later and spray dried. The spray dryer (APV Crepaco, Tonawanda, N.Y.) inlet and exit air temperatures were typically 194° C. and 115° C., respectively. The remainder of the product in the high-shear mixer was pumped directly into the spray dryer to dry. The spray dryer inlet and exit air temperatures were typically 185° C. and 110° C., respectively. The DE value of the product was 3.2.

Example 9

Characterization of Starch-based Opacifying Agent

A. Titanium Dioxide Assay

The titanium dioxide content of the starch-based opacifying agent was estimated by employing a total ash method that is applicable to starches, dextrins and other modified starches. Association of Official Analytical Chemists, Official Methods of Analysis, 13th ed. Secs. 31.102, p. 508, 31,215, p. 534 (1980).

B. Dextrose Equivalent (DE) Assay

The extent of hydrolysis in the starch-based opacifying agent was measured by the School method of dextrose equivalent (Method C-21, Standard Analytical Methods of Grain Processing Corporation). Approximately 1 gram of sample was placed in a 125 ml Erhlenmeyer flask and diluted with water to approximately 30 ml. An empty flask was also filled with approximately 30 ml water. Twenty ml of Fehling solution was added to each flask and the flasks were boiled for 5 minutes. Ten ml of 1.8M potassium iodide solution and 10 mls of 6N sulfuric acid were added to each flask. Approximately 1 ml of 1% soluble starch solution was added to each and the flasks were titrated with 0.1N sodium thiosulfate until the contents changed in color from dark blue to milky white. The dextrose equivalent was calculated by the following equation:

$$DE = \frac{(\text{mls titerated for sample} - \text{mls titerated for blank}) \times (0.3195)}{(\text{Sample weight in grams}) \times (\% \text{ starch in sample})}$$

C. Brookfield Viscosity

Gels (3% on a solids basis; s.b.) of the starch-based opacifying agent were prepared by blending 4.8 grams (s.b.) starch-based opacifying agent and 156 grams of water in a Waring blender at 92° C. at high speed for five minutes. The resultant slurry was poured into 160 ml beaker, covered and held at 4° C. overnight. Subsequently the viscosity was determined employing a Brookfield viscometer model DV-II+. To ensure homogeneity, the sample was first mixed with Brookfield spindle #2 at 100 rpm for 15 seconds. The spindle was changed to #6 and after shearing the sample for 30 seconds at 50 rpm the measurement was recorded in Brookfield centipoise (cP).

D. Scanning Electron Microscopy

A gel (10% on a solids basis) of the starch-based opacifying agent was prepared by blending the appropriate amount of ingredient and water in a Waring blender at 92° C. at high speed for five minutes. The resultant slurry was poured into sample cups and held at 4° C. overnight. The gel sample was spread using a spatula onto a brass block which had been cooled with liquid nitrogen. Subsequent to freezing, the sample was fractured into 3–5 mm pieces using a razor blade which had been cooled in liquid nitrogen. The pieces were then stored in 100% ethanol at −10° C. for 12–18 hours and the ethanol was exchanged 3–5 times. Samples were then critical point dried using $CO_2$ as the transition fluid. Finally, samples were mounted on specimen stubs with colloidal graphite adhesive and sputter-coated with 15–25 nm gold-palladium (60:40). Samples were then imaged at between 1 and 10 KV using an AMR-1000 scanning electron microscope.

E. Characterization of Starch-based Opacifying Agent

The starch-based opacifying agent prepared according to Example 2 was evaluated employing the methods described in A through D. The titanium dioxide content, which is responsible for the opacifying strength of the product, was 15% which is optimal for the coffee creamer application. The starch-based opacifying agents have been produced at titanium dioxide concentrations ranging between 7% and 22% depending on the level of opacity desired in the end product. The DE was determined to be 5.0. Opacifying agents have been produced that exhibit DE's ranging between 2.5 and 5.1 depending on the processing pH which ranged between 4.5 and 3.5, respectively. The Brookfield viscosity which is highly dependent on the DE of the opacifying agent was 40 cP and has been shown to range as high as 900 cP for an opacifying agent exhibiting a DE of 2.5. The microstructure of the starch-based opacifying agent, as characterized by SEM can be described as a semi-continuous gel network which is devoid of starch granules or granule fragments. The discontinuous portions of the network appear as irregularly-shaped microparticles. The titanium dioxide particles are intimately incorporated into the starch matrix and little, if any, free titanium particles can be observed.

Example 10

Preparation of Low Fat Coffee Creamer Containing Starch-based Opacifying Agent

A low fat coffee creamer was prepared with the starch-based opacifying agent produced in Example 2 using the following formula:

| Ingredient | Weight Percentage |
| --- | --- |
| Water | 79.685 |
| Maltodextrin (M100, Grain Processing Corp.) | 15.000 |
| Sodium Stearoyl Lactylate (Breddo #245) | 0.100 |
| Polysorbate 60 (Tween 60, ICI Americas, Inc.) | 0.015 |
| Sodium Caseinate (Alanate 110, New Zealand Milk Products) | 1.500 |
| Dipotassium Phosphate (Food Materials Corp.) | 0.300 |
| Carrageenan (Viscarin GP 109, Food Materials Corp.) | 0.050 |
| Coconut Oil (92° F.) | 2.000 |
| Starch-based Opacifying Agent | 1.350 |
| Total | 100.000 |

The starch-based opacifying agent was slowly added to 205°–210° F. (96°–99° C.) water while mixing with a kitchen blender (high speed) until dispersed. The phosphate was added and dispersed with mixing. Next, maltodextrin, caseinate and carrageenan were added as a dry blend with continued mixing to disperse. The pre-melted oil/emulsifier blend was then added and dispersed into the liquid mixture. Formulation was pasteurized at 185° F. (85° C.) for 60 seconds, then immediately homogenized through a Gaulin two-stage Gaulin homogenizer (2500/500 psi).

Example 11

Characterization of Low Fat Coffee Creamer Containing a Starch-based Opacifying Agent
A. Whiteness in Coffee A Hunter ColorQuest 45/0 colorimeter (Hunter Associates Laboratory, Inc., Reston, Va.) was used to determine the whitening power of the creamer. One ml of the creamer was added to 9 ml of coffee at 80° C. in a small diameter disposable plastic Petri dish and covered with the larger part of the Petri dish and placed on the Hunter ColorQuest port for color analysis. The Hunter ColorQuest was operated employing the following parameters: angle; 10 degrees; light; daylight; scale; CIE lab. The L* -value, which represents whiteness of the analyte, was used to measure whitening power of the creamer after its addition to hot coffee.
B. Brookfield Viscosity The Brookfield viscosity was determined for creamers that were prepared and held at 4° C. for 48 hours. Two hundred ml of a creamer was transferred into a 250 ml beaker and was equilibrated at 20° C. in a water bath for 1 hour. The viscosity of the creamer was measured with a Brookfield viscometer model DV-II+. After the creamer was sheared for 30 seconds at 100 rpm with spindle #2, the viscosity was recorded in Brookfield centipoise.
C. Stability in Coffee This method was used to determine the stability of the creamer when added to coffee at 80° C. In this method 10 ml of creamer prepared as described above was added to 90 ml coffee at 80° C. in 100 ml graduated cylinders, mixed thoroughly and observed over 1 hour period. The formation of the precipitate was noted and the graduation mark on the graduated cylinder was recorded as precipitate volume. The results were expressed as percent stability in coffee as follows:

$$\% \text{ Stability in Coffee} = \frac{(\text{Initial Volume} - \text{Volume of Precipitate}) \times 100}{\text{Initial Volume}}$$

D. Apparent Emulsion Stability

One hundred ml of a creamer was transferred into a 100 ml volumetric cylinder and refrigerated at 4° C. After three weeks, the volume of the opaque phase was measured directly and expressed as a percentage of the initial volume. For example, if no phase separation was observed for the sample it would exhibit a 100% apparent emulsion stability.
E. Titanium dioxide Stability Fifty ml of a creamer was transferred into a 50 ml centrifuge tube and placed vertically in refrigerator at 4° C. At the appropriate times the centrifuge tube was carefully removed from the refrigerator and placed in a freezer at −20° C.

The frozen contents of the centrifuge tube was separated into 3 equal sections from top to bottom and each sample was analyzed for titanium dioxide concentration according to the Leone method (Journal of AOAC, vol. 56, no. 3, 1973, J. L. Leone, "Collaborative Study of the Quantitative Determination of Titanium Dioxide in Cheese"). The titanium dioxide stability was expressed as the percentage of excess titanium dioxide in the bottom section of the centrifuge tube relative to the initial concentration of titanium dioxide in the creamer as follows:

$$\% \text{ Excess TiO}_2 = \frac{([\text{TiO}_2] \text{ Bottom} - [\text{TiO}_2] \text{ initial})}{[\text{TiO}_2] \text{ initial}}$$

F. Titanium Dioxide Resuspendability/Deposition

Fifty ml of a creamer was transferred into a 150 ml metal beaker and placed in a refrigerator at 4° C. At the appropriate time the metal beaker was removed from the refrigerator and shaken moderately by hand for 15 seconds. The decantable content of the beaker was transferred into a 50 ml centrifuge tube and stored in a freezer at −20° C. until titanium dioxide analysis could be performed according to the Leone method (Journal of AOAC, vol. 56, no. 3, 1973, J. L. Leone, "Collaborative Study of the Quantitative Determination of Titanium Dioxide in Cheese"). The titanium dioxide resuspended after a 3 week period was expressed as a percentage of the initial concentration of titanium dioxide as follows:

$$\% \text{ TiO}_2 \text{ Resuspended} = \frac{([\text{TiO}_2] \text{ Resuspended after 3 weeks})}{[\text{TiO}_2] \text{ initial}}$$

G. Characterization of Low Fat Coffee Creamer Containing Starch-based Opacifying Agent The creamer containing the starch-based opacifying agent prepared according to Example 2 was evaluated employing the methods described above in A through F. The following properties of the creamer were measured initially within 2–3 days of production: whiteness, and stability in coffee and viscosity.

The L value of the coffee after the addition of the creamer was 45. This value is lower than that observed for a commercially available Half and Half product (L value=49) and significantly higher than that observed for commercially available no-fat products (L values=37–41). The opacifying strength of the creamer is determined by the titanium dioxide content of the starch-based opacifying agent which can be adjusted to meet the desired degree of whiteness in the coffee. The whitening power of the creamer in coffee is directly proportional to the titanium dioxide concentration of the starch-based opacifying agent as shown in FIG. 1. A whitening power equivalent to that of Half and Half can be achieved with an opacifying agent containing 18–20% titanium dioxide.

Figure 2:
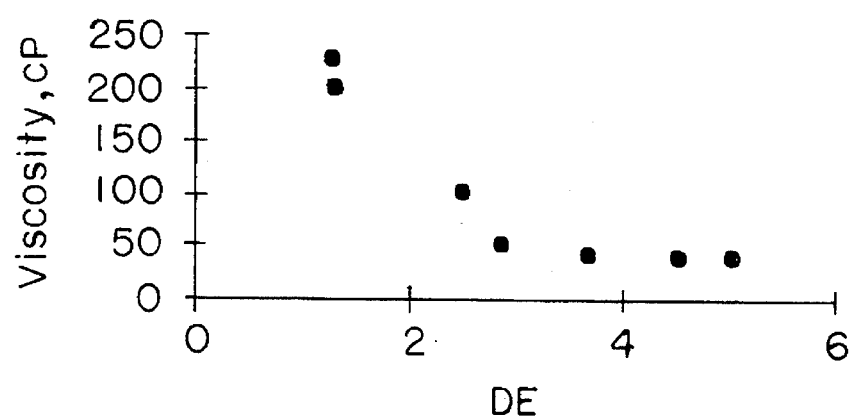
FIG. 2 is a graph showing creamer viscosity versus the dextrose equivalent (DE) of the starch-based opacifying agent.
Figure 3:
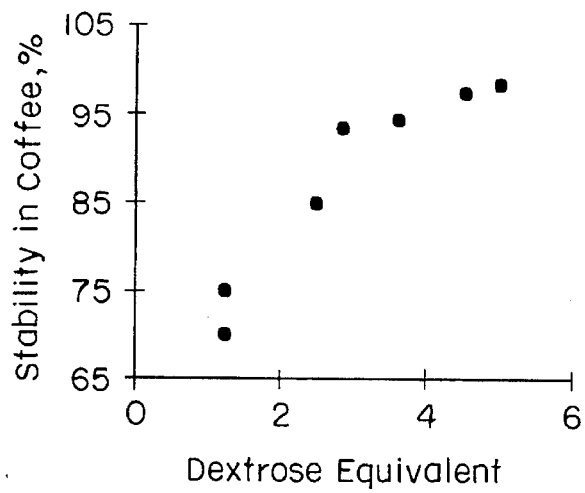
FIG. 3 is a graph showing stability of creamers in coffee as a function of dextrose equivalent of the starch-based opacifying agent.

The Brookfield viscosity of the creamer was determined to be 41 cP which is close to that observed for Half and Half (44 cP) and higher than that observed for a commercially-available no-fat creamer (33 cP). The relationship between the Brookfield viscosity of the creamer and the DE of the starch-based opacifying agent is shown in FIG. 2. The Brookfield viscosity of the creamer decreases linearly as DE increases between 1 and 3. However, the viscosity of the creamer is independent of DE and relatively constant between values of 3 and 5. The optimal viscosity of the creamer is between 40 and 50 cP. The creamer exhibited a 98% stability in over a 1 hour period and did not exhibit any sign of flocculation for at least 30 minutes. As shown in FIG. 3, the stability of the creamer in coffee increases with a concomitant increase in the DE of the opacifying agent. Acceptable stability is observed between a DE of 3 and 5 with an optimal stability being attained at DE=5.0.

The stability of the creamer per se was evaluated over a 3 week period for the following characteristics: apparent emulsion stability, titanium dioxide stability, titanium dioxide resuspendability/deposition and sensory stability.

Figure 4:
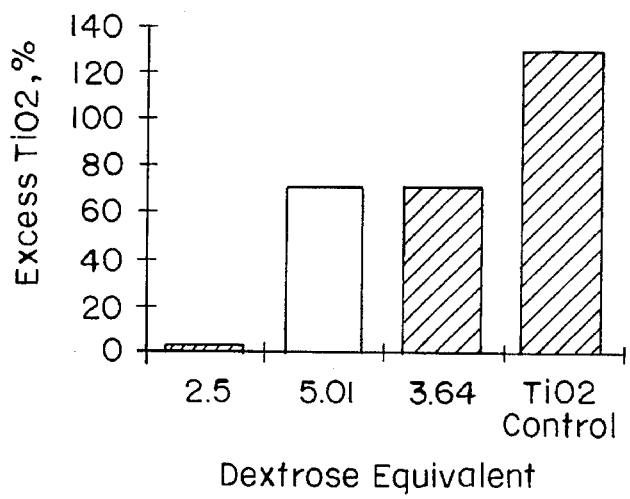
FIG. 4 is a graph showing excess titanium dioxide on the bottom section of a centrifuge tube as a function of the starch-based opacifying agent's dextrose equivalent relative to a control creamer prepared with titanium dioxide but without the starch-based opacifying agent.

As shown in FIG. 4, the starch-based opacifying agent inhibits the sedimentation of titanium dioxide over the range of DE's evaluated relative to a control creamer which contained titanium dioxide did not contain the starch-based opacifying agent. Inhibition increases as the DE of the starch-based opacifying agent decreases and titanium dioxide sedimentation is virtually eliminated when the DE of the starch-based opacifying agent is 2.5 or greater.

Figure 5:
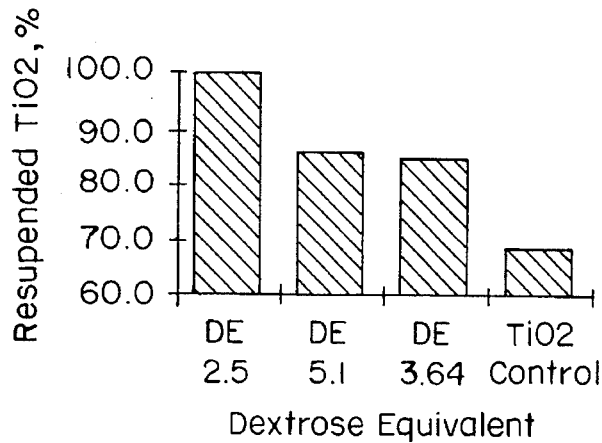
FIG. 5 is a graph showing the resuspendability of titanium dioxide in coffee creamer as a function of the dextrose equivalent of the starch-based opacifying agent and relative to a control creamer prepared with titanium dioxide but without the starch-based opacifying agent.

As shown in FIG. 5, the resuspendability of titanium dioxide shows a similar relationship to the DE of the starch-based opacifying agent. Relative to the control which did not contain the starch-based opacifying agent, the starch-based opacifying agent over the range of DE's tested did enhance titanium dioxide resuspendability by inhibiting the deposition of titanium dioxide. Titanium dioxide deposition is virtually eliminated when the DE of the starch-based opacifying agent is 2.5 or greater. This experiment was also carried out with the separate titanium dioxide and starch components of the opacifying agent (DE=2.5), uncomplexed and simply formulated into a creamer. This sample exhibited significant titanium dioxide deposition that was similar to that observed for the titanium dioxide control. This experiment demonstrates the importance of the complex form of the ingredient to prevent titanium dioxide deposition.

Sensory evaluations were also performed on opacifying agents ranging between 2.5 and 5.1. Over the three week period, no significant differences in overall appearance, mouth viscosity or mouthfeel were observed.

Example 12

Preparation of a Low-Fat Cottage Cheese Dressing with Starch-based Opacifying Agent A low fat dressing was prepared with the starch-based opacifying agent produced according to Example 4 using the following formulation:

| Ingredient | Weight Percentage |
| --- | --- |
| Starch-based Opacifying Agent | 1.60 |
| Heavy Cream | 1.30 |
| Non-Fat Dry Milk | 13.90 |
| Salt | 2.00 |
| Water | 81.20 |
| | 100.00 |

Water was heated to 100° C. (212° F.) in a water bath equipped with an LIGHTNIN™ overhead mixer. Temperature was maintained at 95° C. (203° C.) while the dry ingredients (as a blend) were slowly added to the water with constant mixing (800 rpm). Once the dries were dispersed, cream was added followed by pasteurization (74° C.; 165° F.) for 30 minutes, all the while slowly stirring with the overhead mixer. The dressing was subsequently homogenized by passing through a two-state gaulin homogenizer (2000/500 psi). The product was cooled and stored refrigerated.

Finished dressing was used to make cottage cheese by mixing with dry curds. The resulting product was visually similar to the full-fat product with the viscosity and mouthfeel expected from full fat without any signs of titanium settling out in the containers.

In a control experiment the individual components of the opacifying agent were added as a dry blend and formulated and processed as above. Resultant dressings were held under refrigerated storage. After only two days, the dressing with the individual component ingredients showed signs of instability (white sediment on the bottom of test tube) while the sample prepared with the opacifying agent showed no sediment.

Equivalents

Those skilled in the art will recognize, or be able to ascertain using no more than routine experimentation, many equivalents to the specific embodiments of the invention described herein. Such equivalents are intended to be encompassed by the following claims:

We claim:

1. A starch-based opacifying agent consisting essentially of starch, an opacifying agent and optional additive selected from the group consisting of excipients, flavors, sugars, lipids, colors and combinations thereof, in the form of a complex in which the opacifying agent is incorporated into the starch matrix.

2. The starch-based opacifying agent of claim 1 wherein the opacifying agent is selected from the group consisting of titanium dioxide, aqueous insoluble inorganic compounds, aqueous insoluble organic compounds and insoluble proteins.

3. The starch-based opacifying agent of claim 2 wherein the inorganic compound is selected from the group consisting of magnesium salts, barium salts and calcium salts.

4. Non-dairy creamer containing the opacifying agent of claim 1.

5. A cosmetic containing the opacifying agent of claim 1.

6. A lotion or cream containing the opacifying agent of claim 1.

7. A non-food formulation containing the opacifying agent of claim 1.

8. The starch-based opacifying agent of claim 1 wherein the starch/opacifying agent has a dextrose equivalent of from about 2.5 to about 6.0.

9. The starch-based opacifying agent of claim 1 wherein the starch is a high amylose starch that has been pregelatinized under aqueous conditions.

10. A food or beverage formulation containing a starch-based opacifying agent consisting essentially of starch, an opacifying agent and optional additive selected from the group consisting of excipients, flavors, sugars, lipids, colors and combinations thereof, in the form of a complex in which the opacifying agent is incorporated into the starch matrix.

11. The food or beverage formulation of claim 10 wherein the food or beverage is selected from the group consisting of coffee creamer, cottage cheese dressing, nutritional beverages, mayonnaise, sour cream, ice cream, yogurt and salad dressing.

12. The food or beverage formulation of claim 10 that contains a reduced fat content or is fat free.

13. The food or beverage formulation of claim 10 wherein the opacifying agent is selected from the group consisting of titanium dioxide, aqueous insoluble inorganic compounds, aqueous insoluble organic compounds and insoluble proteins.

14. The food or beverage formulation of claim 13 wherein the inorganic compound is selected from the group consisting of magnesium salts, barium salts and calcium salts.

15. The food or beverage formulation of claim 10 wherein the starch/opacifying agent has a dextrose equivalent of from about 2.5 to about 6.0.

16. The food or beverage formulation of claim 10, wherein the starch is a high amylose starch that has been pregelatinized under aqueous acid conditions.

17. A starch-based opacifying agent consisting essentially of starch, maltodextrin, titanium dioxide and optional additive selected from the group consisting of excipients, flavors, sugars, lipids, colors and combinations thereof, in the form of a complex in which the opacifying agent is incorporated into the starch matrix.

18. A food or beverage formulation containing a starch-based opacifying agent consisting essentially of starch, maltodextrin, titanium dioxide and optional additive selected from the group consisting of excipients, flavors, sugars, lipids, colors and combinations thereof, in the form of a complex in which the opacifying agent is incorporated into the starch matrix.

19. A food or beverage formulation containing a starch-based opacifying agent consisting essentially of starch, an opacifying agent and optional additive selected from the group consisting of excipients, flavors, sugars, lipids, colors and combinations thereof, in the form of a complex in which the opacifying agent is incorporated into the starch matrix, wherein the starch-based opacifying agent is produced by a method comprising the steps of:

a) heating a slurry of high amylose starch in an acidic aqueous medium for a temperature, pressure and time sufficient to substantially disrupt starch granules, to produce a solubilized starch solution;

b) filtering the resultant starch solution to remove impurities;

c) optionally adding an additive prior to or after step (b); and d) adding an opacifying agent to the filtered an solubilized starch solution under agitating conditions thereby producing the starch-based opacifying agent.

20. The food or beverage formulation of claim 19 wherein the high amylose starch is derived from corn, oat, barley or pea.

21. The food or beverage formulation of claim 19 wherein the slurry comprises from about 1 to about 30% (w/v) high amylose starch.

22. The food or beverage formulation of claim 21 wherein the slurry comprises from about 5 to about 15% (w/v) high amylose starch.

23. The food or beverage formulation of claim 19 wherein step (a) is performed at a final temperature from about 125° C. to about 160° C.

24. The food or beverage formulation of claim 23 wherein the slurry is heated to a final temperature of about 138° C. and held for from about 40 to about 120 minutes.

25. The food or beverage formulation of claim 19 wherein the slurry has a pH of from about 3.0 to about 4.7.

26. The food or beverage formulation of claim 19 wherein the starch/opacifying agent has a dextrose equivalent of from about 2.5 to about 6.0.

27. The food or beverage formulation of claim 19 wherein the opacifying agent is selected from the group consisting of titanium dioxide, aqueous insoluble inorganic compounds, aqueous insoluble organic compounds and insoluble proteins.

28. The food or beverage formulation of claim 27 wherein the inorganic compound is selected from the group consisting of magnesium salt, barium salts, sodium salts and calcium salts.

29. The food or beverage formulation of claim 27 wherein the opacifying agent is added in an amount of from about 5 to about 50 percent by weight.

30. The food or beverage formulation of claim 19 wherein step (c) is performed at a temperature from about 75° C. to about 95° C.

31. The food or beverage formulation of claim 30 further comprising the step of drying the starch-based opacifying agent into a powder.

32. The food or beverage formulation of claim 19 further comprising the following step:

d) reducing the temperature of the resultant solution to a temperature and period of time sufficient for the starch to retrograde.

33. The food or beverage formulation of claim 19 wherein the solution of step a) is treated with diatomaceous earth and activated charcoal before filtering in step b).

34. The food or beverage formulation of claim 19 wherein step b) is performed by combining the resultant solution with diatomaceous earth and filtering the combination through a carbon impregnated filtration device.

35. The food or beverage formulation of claim 19 wherein step a) is performed by jet cooking the slurry of starch.

36. The food or beverage formulation of claim 19 wherein the complex contains the additive and is selected from the group consisting of maltodextrin, titanium dioxide and combinations thereof.

* * * * *

UNITED STATES PATENT AND TRADEMARK OFFICE
CERTIFICATE OF CORRECTION

PATENT NO. : 5,571,334
DATED : November 5, 1996
INVENTOR(S) : John Michael Dunn, Akiva T. Gross and Eugene Terry Finocchiaro It is certified that error appears in the above-indentified patent and that said Letters Patent is hereby corrected as shown below:

Column 20, Claim 9, line 33, after "aqueous" insert ---acid---.

Column 21, Claim 19, line 24, step (d), after "filtered", delete "an" and insert ---and---.

Signed and Sealed this

Eighteenth Day of February, 1997

Attest:

BRUCE LEHMAN

*Attesting Officer*      *Commissioner of Patents and Trademarks*